(12) United States Patent
Su (10) Patent No.: US 10,813,682 B2
(45) Date of Patent: Oct. 27, 2020

(54) NON-INVASIVE RADIO-FREQUENCY ABLATION SYSTEM

(71) Applicant: Sea-Quan Su, Taipei (TW)

(72) Inventor: Sea-Quan Su, Taipei (TW)

(*) Notice: Subject to any disclaimer, the term of this patent is extended or adjusted under 35 U.S.C. 154(b) by 0 days.

(21) Appl. No.: 16/007,187

(22) Filed: Jun. 13, 2018

(65) Prior Publication Data
US 2019/0059981 A1  Feb. 28, 2019

Related U.S. Application Data

(63) Continuation of application No. 15/688,973, filed on Aug. 29, 2017, now abandoned.

(51) Int. Cl.
*A61B 18/12* (2006.01)
*A61B 18/14* (2006.01)
*A61B 8/12* (2006.01)
*A61B 18/00* (2006.01)
*A61B 18/16* (2006.01)

(52) U.S. Cl.
CPC ............... *A61B 18/14* (2013.01); *A61B 8/12* (2013.01); *A61B 18/1402* (2013.01); *A61B 18/1485* (2013.01); *A61B 18/1492* (2013.01); *A61B 2018/005* (2013.01); *A61B 2018/00011* (2013.01); *A61B 2018/00047* (2013.01); *A61B 2018/00196* (2013.01); *A61B 2018/00327* (2013.01); *A61B 2018/00488* (2013.01); *A61B 2018/00517* (2013.01); *A61B 2018/00577* (2013.01); *A61B 2018/00642* (2013.01); *A61B 2018/00714* (2013.01); *A61B 2018/00738* (2013.01); *A61B 2018/00815* (2013.01); *A61B 2018/1497* (2013.01); *A61B 2018/162* (2013.01)

(58) Field of Classification Search
CPC ............ A61B 18/14; A61B 2018/1467; A61B 2018/1485; A61B 2018/00577
See application file for complete search history.

(56) References Cited

U.S. PATENT DOCUMENTS 6,004,269 A * 12/1999 Crowley .............. A61B 8/4461
                                                    600/374
6,081,749 A *  6/2000 Ingle .................. A61B 18/1485
                                                    606/41
6,109,268 A *  8/2000 Thapliyal ........... A61B 18/1485
                                                    128/898

(Continued)

*Primary Examiner* — Daniel W Fowler
(74) *Attorney, Agent, or Firm* — Bacon & Thomas, PLLC (57) ABSTRACT

An ablation device of a non-invasive radio-frequency ablation system includes a substrate having a first surface; a first electrode disposed on the first surface; a second electrode disposed on the first surface and adjacent to the first electrode; a moving unit electrically connected to the second electrode for moving the second electrode to regulate the distance between the second electrode and the first electrode; and a radio frequency generator connected to the ablation device for providing a radio frequency current to the first electrode and the second electrode. According to a method using the ablation device, the first and second electrodes are brought into contact with a third surface belonging to a subject in need of treatment, and the radio frequency current is applied to the electrodes to carry out a treatment procedure. The treatment depth and area are adjusted by changing the relative distance between the electrodes.

7 Claims, 12 Drawing Sheets

(56) References Cited

U.S. PATENT DOCUMENTS

| | | | | | |
|---|---|---|---|---|---|
| 6,152,924 | A | * | 11/2000 | Parins | A61B 18/1445 606/174 |
| 6,178,354 | B1 | * | 1/2001 | Gibson | A61B 18/1492 607/116 |
| 6,413,255 | B1 | * | 7/2002 | Stern | A61B 18/14 606/41 |
| 6,464,699 | B1 | * | 10/2002 | Swanson | A61B 17/00234 606/32 |
| 2003/0009164 | A1 | * | 1/2003 | Woloszko | A61B 18/1402 606/41 |
| 2008/0195090 | A1 | * | 8/2008 | Takashino | A61B 18/1445 606/41 |
| 2009/0299361 | A1 | * | 12/2009 | Flyash | A61B 18/14 606/33 |
| 2010/0022999 | A1 | * | 1/2010 | Gollnick | A61B 18/1402 606/33 |
| 2014/0039491 | A1 | * | 2/2014 | Bakos | A61B 18/1492 606/41 |

* cited by examiner

NON-INVASIVE RADIO-FREQUENCY ABLATION SYSTEM

BACKGROUND OF THE INVENTION

1. Field of the Invention

The present disclosure relates to a non-invasive radio-frequency ablation (RFA) system and a method for treating mucosal or soft tissue related diseases and, more particularly, to a method for treating tubular soft tissue related diseases.

2. Description of Related Art

Radio-frequency ablation (RFA) is one of the most commonly used methods in surgical treatment. It can be applied in a variety of fields such as treatment of liver cancer, lung cancer and other tumors, thyroid nodules, and heart disease, in plastic surgery, and in otolaryngology for treatment of chronic hypertrophic rhinitis, chronic hypertrophic pharyngitis, and patients with sleep snoring . . . etc.

In RFA, an electrode on a metal probe (so call mono-polar RFA) or two probes with electrodes situated at a fixed-distance (so call bipolar RFA) are inserted into a tissue, and used to heat up the tissue between the two electrodes by introducing a current at a specific frequency to achieve the purpose of ablating lesions.

Although RFA is widely used nowadays, there are still many issues with this technique. For instance, prolonged treatment will cause thermal damage or necrosis to peripheral non-targeted tissue; and in the case of bi-polar RFA, the depth of treatment is limited by the distance between the two-electrodes. In addition, most of the current RFA treatment techniques are invasive and accompanied with bleeding, treatment surface hemorrhage, thermal damage to peripheral non-targeted tissue and the risk of infection.

Therefore, it is necessary to develop a non-invasive radio-frequency treatment that can effectively and precisely control the RF treatment area, depth, and temperature, and simultaneously eliminate the thermal damage to the surrounding tissue.

SUMMARY OF THE INVENTION

According to one aspect, the present invention provides a non-invasive radio-frequency ablation system that does not require insertion of electrodes into tissues, and thereby eliminating bleeding or perforation at the lesion position, which reduces the risk of treatment complications. The electrodes used in the non-invasive RFA system are adjustable rather than fixed, so that the treatment depth can be changed by regulating the distance between the electrodes.

According to another aspect, the present invention provides a method of performing non-invasive radio-frequency ablation that does not require insertion of electrodes into tissues, and which uses adjustable electrodes to change the treatment depth.

According to another aspect, the present invention may optionally comprise a tissue contact cooling unit that can lower the contact tissue surface temperature .and increase the impedance of the contact tissue surface. The contact cooling unit will not only spare the contact tissue surface from thermal damage but also increase the RF flow and thermal ablation effect at a deeper layer during treatment. In addition, in order to enhance the therapeutic effects, the device of the present disclosure may optionally have a temperature sensing unit and/or a treatment depth sensing unit to sense the temperature and/or treatment depth so as to enhance the therapeutic effect.

According to an exemplary preferred embodiment of the invention, the non-invasive radio-frequency ablation system includes an ablation device comprising: a substrate having a first surface; a first electrode disposed on the first surface; a second electrode disposed on the first surface and adjacent to the first electrode; a moving unit electrically connected to the second electrode, to regulate the distance between the second electrode and the first electrode by moving the second electrode; and a radio frequency generator connected to the ablation device for providing a radio frequency current to the first electrode and the second electrode.

According to another exemplary preferred embodiment of the invention, an non-invasive radio-frequency ablation method for treating soft or mucosal tissue related diseases comprises the following steps: (A) providing a non-invasive radio-frequency ablation system that includes an ablation device, the ablation device comprising: a substrate having a first surface; a first electrode disposed on the first surface; a second electrode disposed on the first surface and adjacent to the first electrode; a moving unit electrically connected to the second electrode and moving the second electrode to regulate the distance between the second electrode and the first electrode; and a radio frequency generator connected to the ablation device; (B) contacting the ablation device with a third surface of a subject in need; and (C) providing a radio frequency current to the first electrode and the second electrode by, the radio frequency generator and producing thermal energy to ablate or electrically burn the soft or mucosal tissue under the third surface.

In the method of the above-described exemplary preferred embodiment, step (B) or step (C) may be further followed by a step (D) of moving the second electrode to regulate the distance between the second electrode and the first electrode and thereby regulate the treatment depth at the area beneath the first electrode and the second electrode.

Additional preferred embodiments may include one or more of the following features:

The moving unit of the radio-frequency ablation system, which regulates the distance between the second electrode and the first electrode may, by way of example and not limitation, be a ball screw. In addition, the moving unit can be driven in any manner, such as by a motor.

An optional cooling unit may be disposed on the first surface and between the first electrode and second electrode to lower the temperature of the targeted tissue surface, and may, by way of example and not limitation, include a cooling chip and/or refrigerant.

The substrate of the ablation device may further comprise a second surface opposite to the first surface, and the ablation device may optionally comprise a temperature sensing unit disposed at any position on the first surface or second surface. For instance, the temperature sensing unit may be disposed on the first surface and between the first electrode and the second electrode or, alternatively, the temperature sensing unit may be disposed on the second surface and opposite to the first electrode. By way of example and not limitation, the temperature sensing unit may be a thermistor or a resistance temperature detector (RTD).

The ablation device having a substrate with a second surface opposite to the first surface, may further comprise a treatment depth unit disposed at any position on the first surface or second surface such as, for instance, on the first surface and between the first electrode and the second electrode or, alternatively, on the second surface and opposite to the position that is between the first electrode and the second electrode. By way of example and not limitation, the treatment depth sensing unit may be an ultrasonic transducer.

The term "subject in need" is not to be limited to a particular subject to be treated, and may refer not only to human subjects but also to non-human mammalian and other subjects. The term "the third surface" used in the present disclosure is not limited to a particular surface, and may include surfaces of any inner tubular area such as the surface of a nasal concha, throat, bronchus, esophagus, urethra, or rectum.

In the present disclosure, the terms "treat," "treating," or "treatment" refers to dealing with abnormal physical conditions such as symptoms, disorders, or diseases in human or animal (i.e., veterinary applications). In general, the terms relate to treatment or therapy that achieves a desired effect such as suppressing an abnormal physical condition. For example, the terms may refer to slowing a disease progress, halting the disease progress, ameliorating a physical abnormal condition, and/or eliminating or relieving at least one symptom related to or caused by the abnormal physical condition, including elimination of one or more symptoms, or complete eradication of a disorder.

Other objects, advantages, and novel features of the disclosure will become more apparent from the following detailed description when taken in conjunction with the accompanying drawings.

DETAILED DESCRIPTION OF THE PREFERRED EMBODIMENTS

Although the present invention has been explained in relation to preferred embodiments, it is to be understood that many other possible modifications and variations can be made without departing from the spirit and scope of the invention.

In addition, ordinal numbers such as "first", "second", "third" and the like used in the specification and claims for modifying elements of the claim do not mean and represent the claimed elements have any antecedent ordinal number, nor do they represent the order (or order of production) between a claimed element. The ordinal numbers are only used to clearly distinguish between certain claimed elements having the same name.

Embodiment 1

Figure 1:
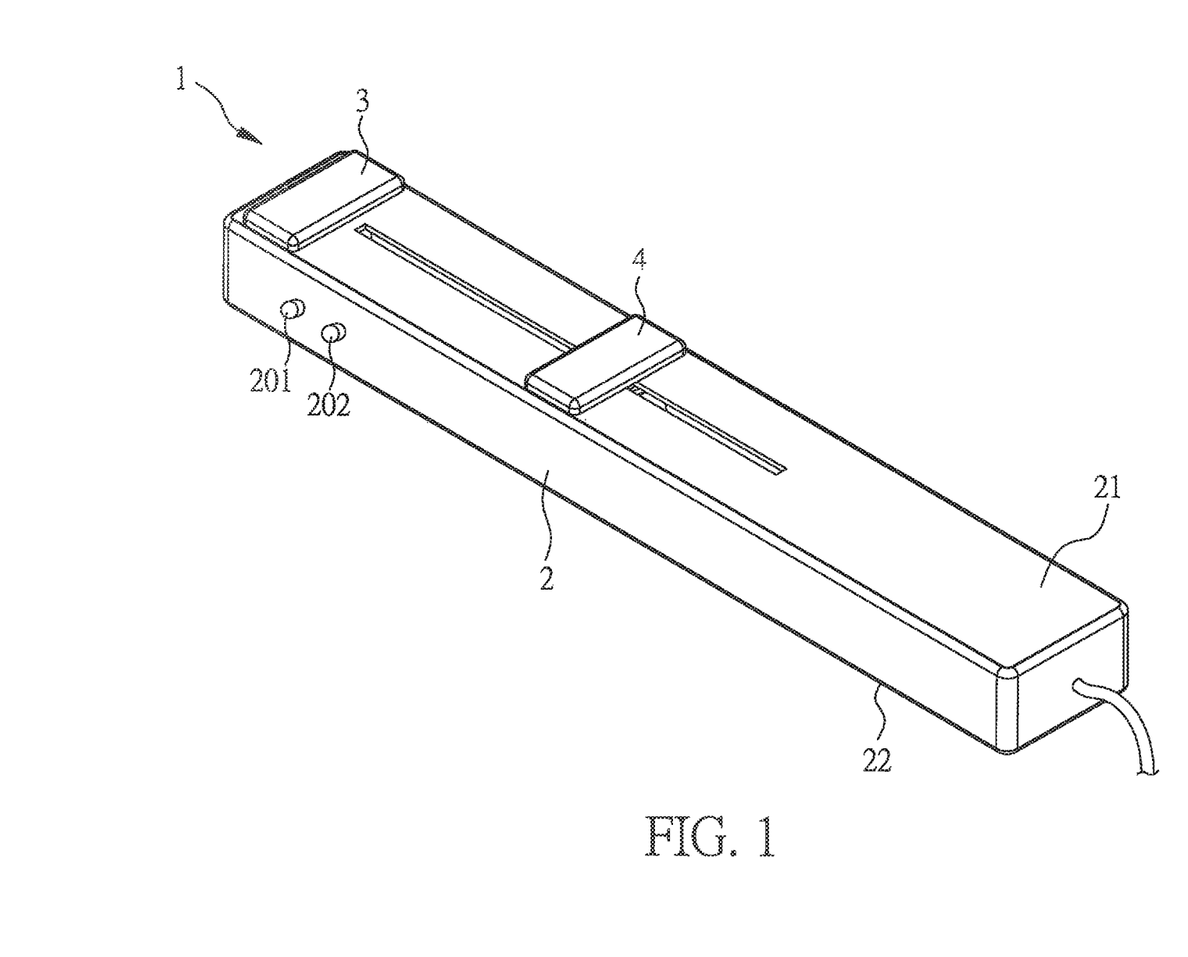
FIG. 1 is a schematic diagram of an ablation device according to a first preferred embodiment of the invention.
Figure 2:
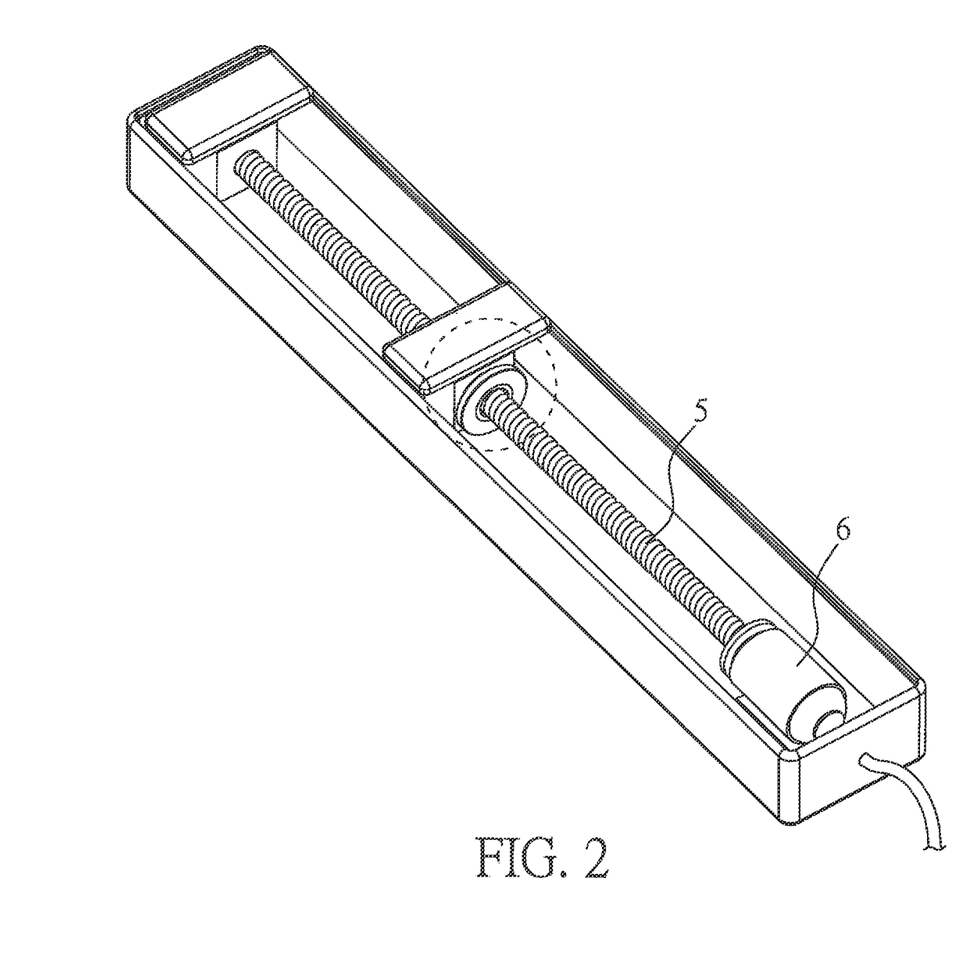
FIG. 2 is a partial schematic diagram of an ablation device according to the first preferred embodiment.
Figure 3:
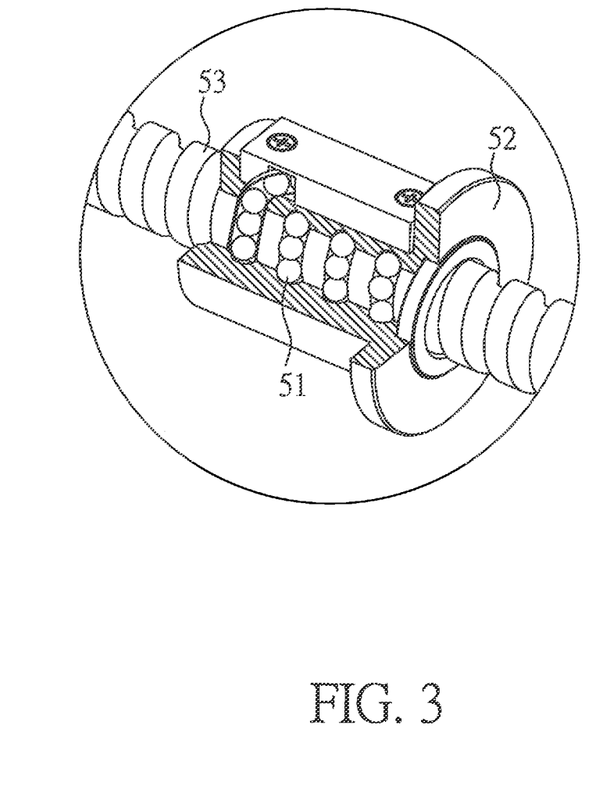
FIG. 3 is a schematic diagram showing partial enlargement of a moving unit according to the first preferred embodiment.

FIG. 1 is a schematic diagram of an ablation device of a first preferred embodiment, FIG. 2 is a partial schematic diagram of the embodiment of FIG. 1; FIG. 3 is a schematic diagram showing a partial enlargement of the moving unit of FIG. 2. This embodiment includes: an ablation device 1 comprising: a substrate 2 having a first surface 21; a first electrode 3 disposed on the first surface 21; a second electrode 4 disposed on the first surface 21 and adjacent to the first electrode 3; a moving unit 5 electrically connected to the second electrode 4 for moving the second electrode 4 to regulate the distance between the second electrode 4 and the first electrode 3; and a radio frequency generator (not shown) connected to the ablation device 1 for providing a radio frequency current to the first electrode 3 and the second electrode 4. The moving unit 5 is a ball screw, as shown in the partial enlargement diagram of FIG. 3. The ball screw 5 improves poor positioning and prevents damage by placing a steel bead 51 between nut 52 and screw rod 53, replacing sliding friction with rolling friction. Furthermore, the ball screw 5 of the present embodiment is driven by a motor 6 to achieve the purpose of moving the second electrode 4.

The substrate may be made of materials selected from any non-conductive materials known in the art such as, but not limited to, plastic, polymer, ceramic material and the like. The first electrode 3 and the second electrode 4 may be made of materials selected from conductive materials known in the art including, but not limited to, metals such as gold, silver, copper, and aluminum or alloys thereof, as well non-metallic conductive materials The shape of the first electrode and the second electrode is not particularly limited and may be circular, rectangular, oval and the like.

Embodiment 2

Figure 4:
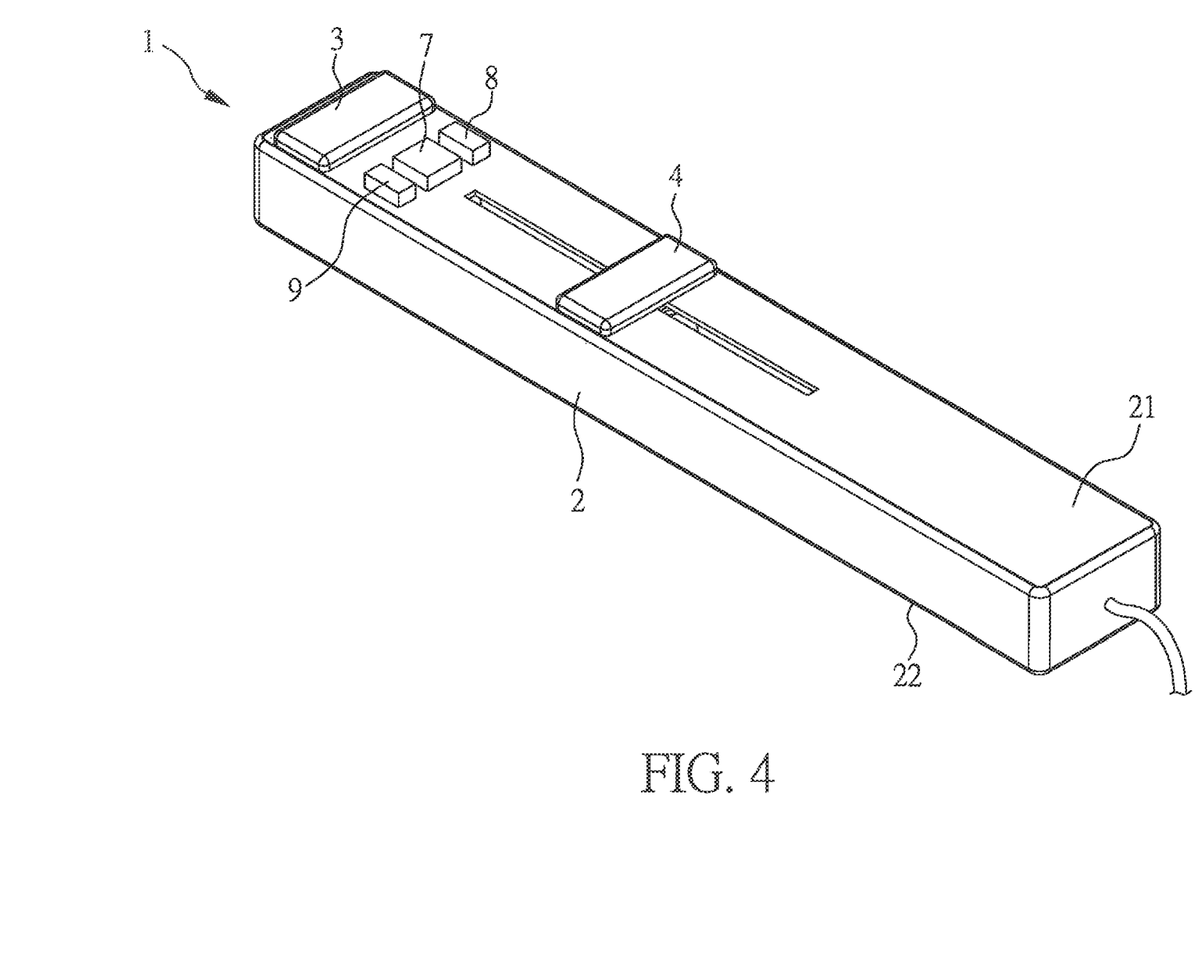
FIG. 4 is a schematic diagram of an ablation device according to a second preferred embodiment.

FIG. 4 is a schematic diagram of an ablation device of another embodiment of the present invention. The ablation device of the non-invasive radio-frequency ablation system in the present embodiment is similar to that of Embodiment 1 except for the following differences.

Referring to FIG. 4, the ablation device in the present embodiment may optionally comprise a cooling unit 7, a temperature sensing unit 8, and a treatment depth sensing unit 9. The cooling unit 7 may be disposed on the first surface 21 of the substrate 2 and between the first electrode 3 and the second electrode 4. In the present embodiment, the ablation device is illustrated as including each of the cooling unit 7, the temperature sensing unit 8 and treatment the depth sensing unit 9. However, any one or more of the cooling unit 7, the temperature sensing unit 8 and treatment depth sensing unit 9 may also be omitted.

The cooling unit 7 may include a cooling chip and/or a refrigerant to lower the temperature of the targeted tissue surface and avoid thermal damage to the targeted tissue surface.

The temperature sensing unit 8 may be disposed on the first surface 21 of the substrate 2 and between the first electrode 3 and the second electrode 4. The temperature sensing unit 8 may be a thermistor or a resistance temperature detector (RTD) to detect the temperature of the treating target area during the treatment. The detected temperature may be used to control the cooling unit so as to enhance the treatment effect.

The treatment depth sensing unit 9 may be disposed on the first surface 21 of the substrate 2 and between the first electrode 3 and the second electrode 4. The treatment depth sensing unit may be an ultrasonic transducer to detect the location of the lesion before, during, and/or after the treatment to increase the accuracy of the treatment by regulating the distance between the first electrode 3 and the second electrode 4, and thus changing the treatment depth to enhance the therapeutic effect.

Embodiment 3

Figure 5:
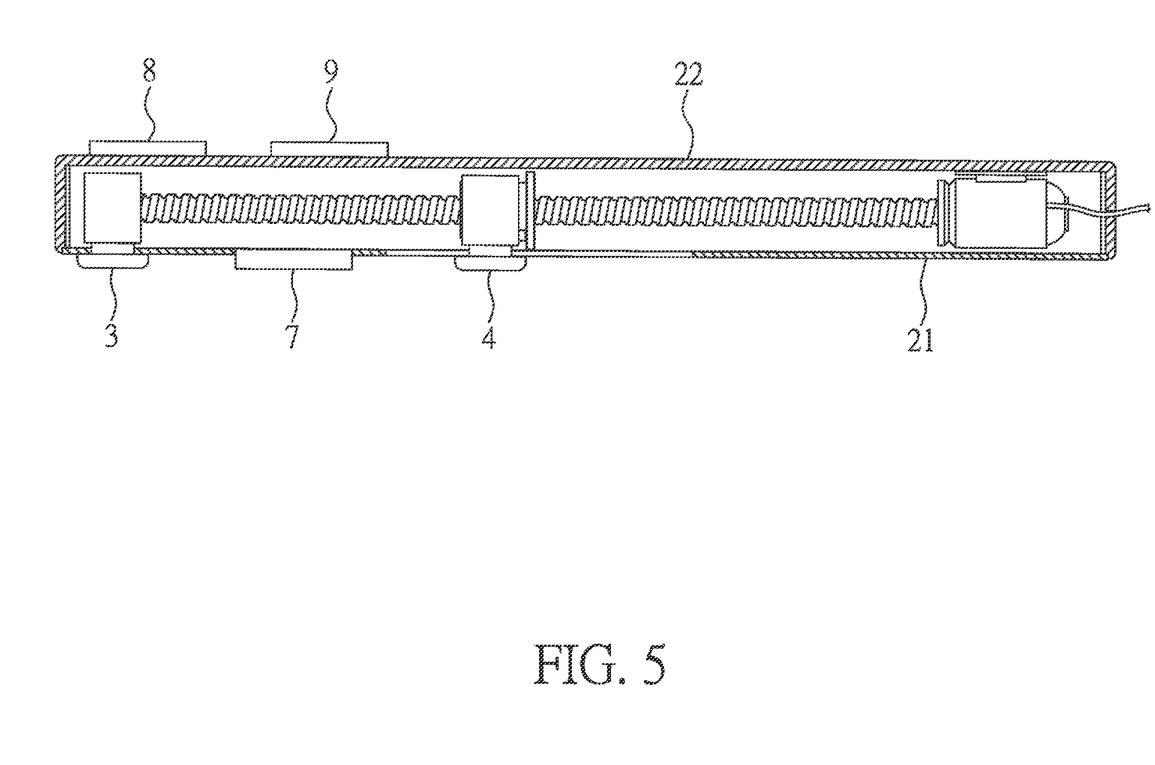
FIG. 5 is a schematic diagram of an ablation device according to a third preferred embodiment.

FIG. 5 is a schematic diagram of an ablation device according to another embodiment of the present invention. The ablation device of the non-invasive radio-frequency ablation system in the present embodiment is similar to that of Embodiment 1 or 2 except for the following differences.

Referring to FIG. 5, the ablation device of the present embodiment may optionally comprise a cooling unit 7, a temperature sensing unit 8, and a treatment depth sensing unit 9. The cooling unit 7 may be disposed on the first surface 21 of the substrate 2 and between the first electrode 3 and the second electrode 4.

The temperature sensing unit 8 may be disposed on the second surface 22 of the substrate 2 and opposite to the first electrode 3, but the location of the temperature sensing unit may be varied without departing from the invention.

The treatment depth sensing unit 9 may be disposed on the second surface 22 of the substrate 2 and opposite to the cooling unit 7, but the location of the treatment depth sensing unit may also be varied.

Embodiment 4

Figure 6:
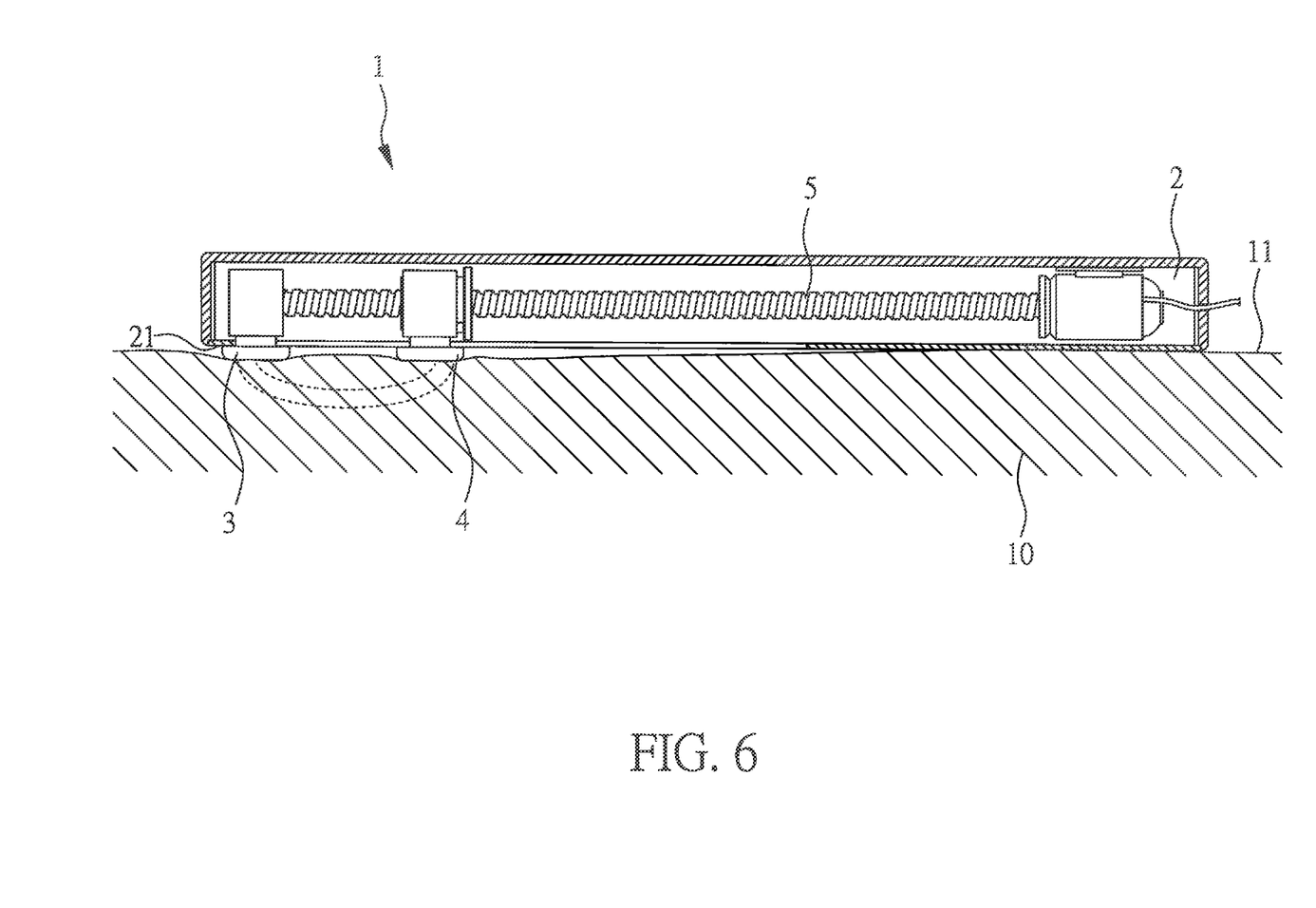
FIG. 6 is a schematic diagram according to a fourth preferred embodiment.
Figure 7:
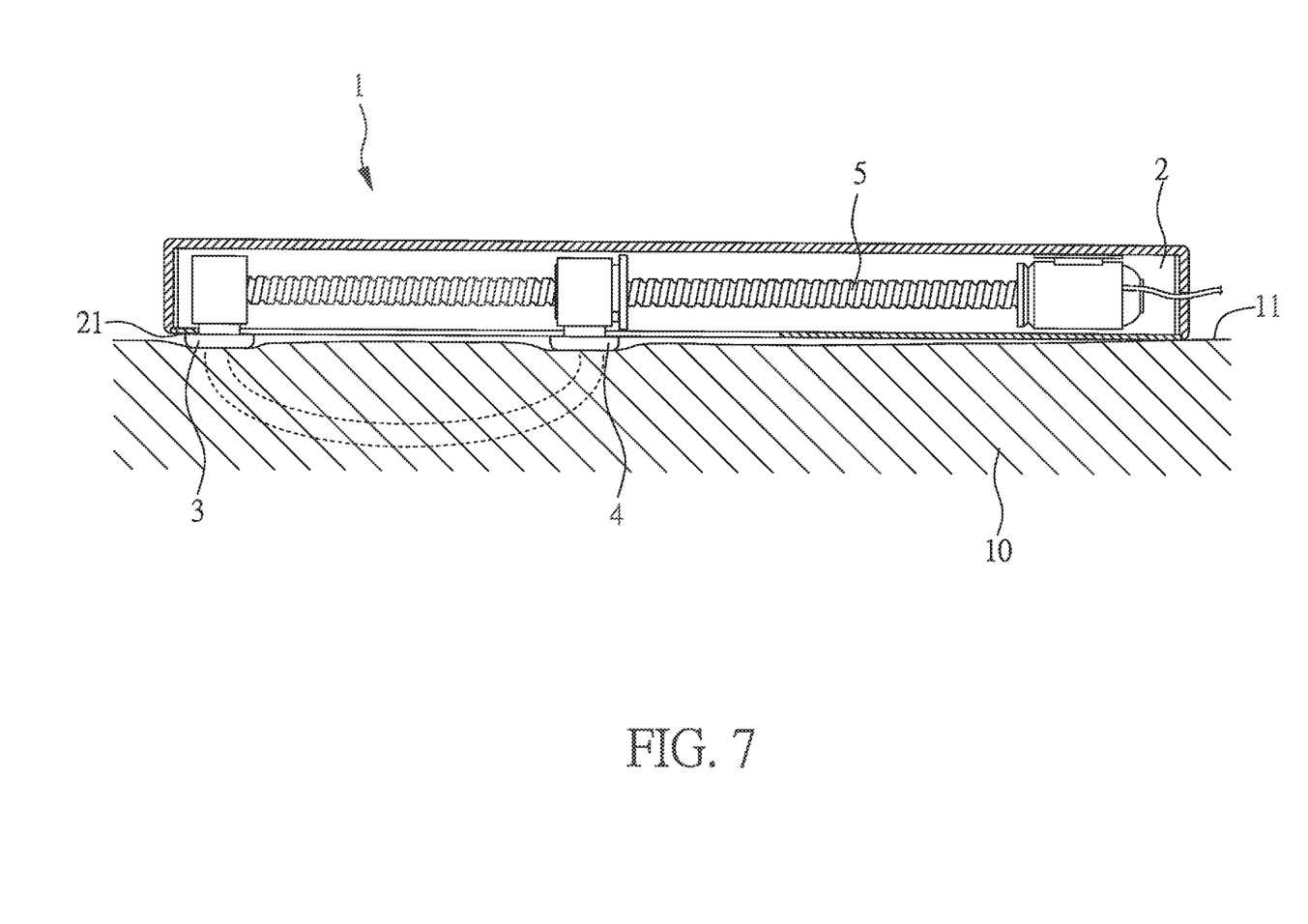
FIG. 7 is another schematic diagram according to a fourth preferred embodiment.

FIGS. 6 and 7 are schematic diagrams that illustrate a treatment method according to a preferred embodiment of the present invention. The first electrode 3 and the second electrode 4 of an ablation device according to the first embodiment are contacted with a third surface 11 of a subject in need 10, and a radio frequency generator (not shown) provides a radio frequency current to the first electrode 3 and the second electrode 4. Thereafter, the radio frequency generates thermal energy between the first electrode 3 and the second electrode 4 to ablate or electrically burn the target lesion tissue under the third surface 11. Although only the ablation device is illustrated in FIGS. 6 and 7, it will be appreciated that the method may also use an ablation that optionally includes cooling unit 7, temperature sensing unit 8 and/or treatment depth sensing unit 9 according to Embodiment 2 or 3.

As shown in FIG. 6, when the distance between the first electrode 3 and the second electrode 4 is relatively short, the penetration of the RF energy is relatively superficial, and the target tissue at the superficial layer will be treated. As shown in FIG. 7, when the distance between the first electrode 3 and the second electrode 4 is relatively long, the penetration of the RF energy is relatively deeper, and the target tissue located in the deeper layer will be treated. The RF energy penetration depth is equal to the distance between the first electrode 3 and the second electrode 4 divided by 2.

Since the ablation device of the present disclosure comprises the adjustable electrode, the treatment depth can be changed by regulating the distance of the two electrodes. Compared with the traditional techniques, the present system and method can be applied over a wider range and reduce complications in operation.

Embodiment 5

Figure 8:
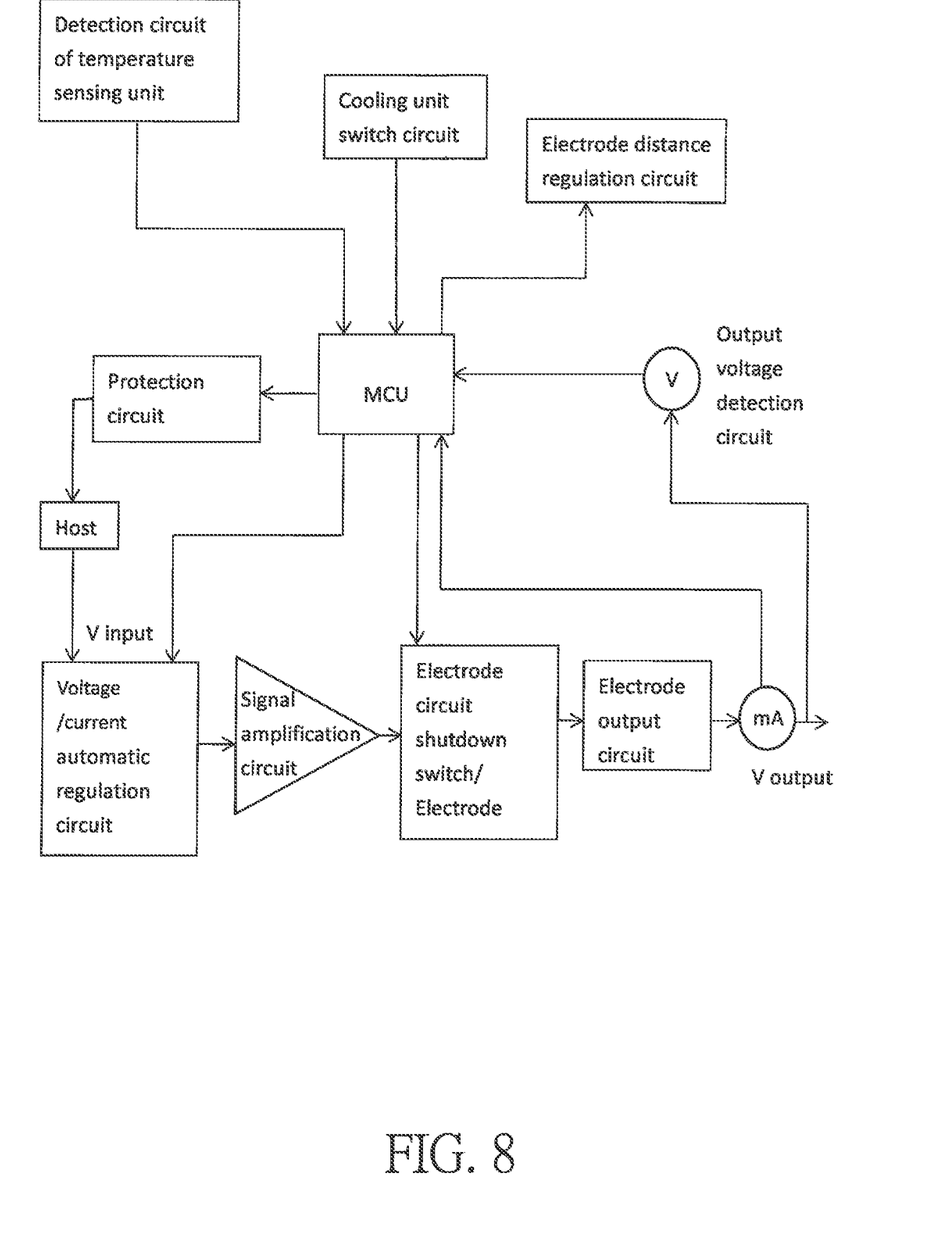
FIG. 8 is a block diagram of a system operation of a preferred embodiment.
Figure 9:
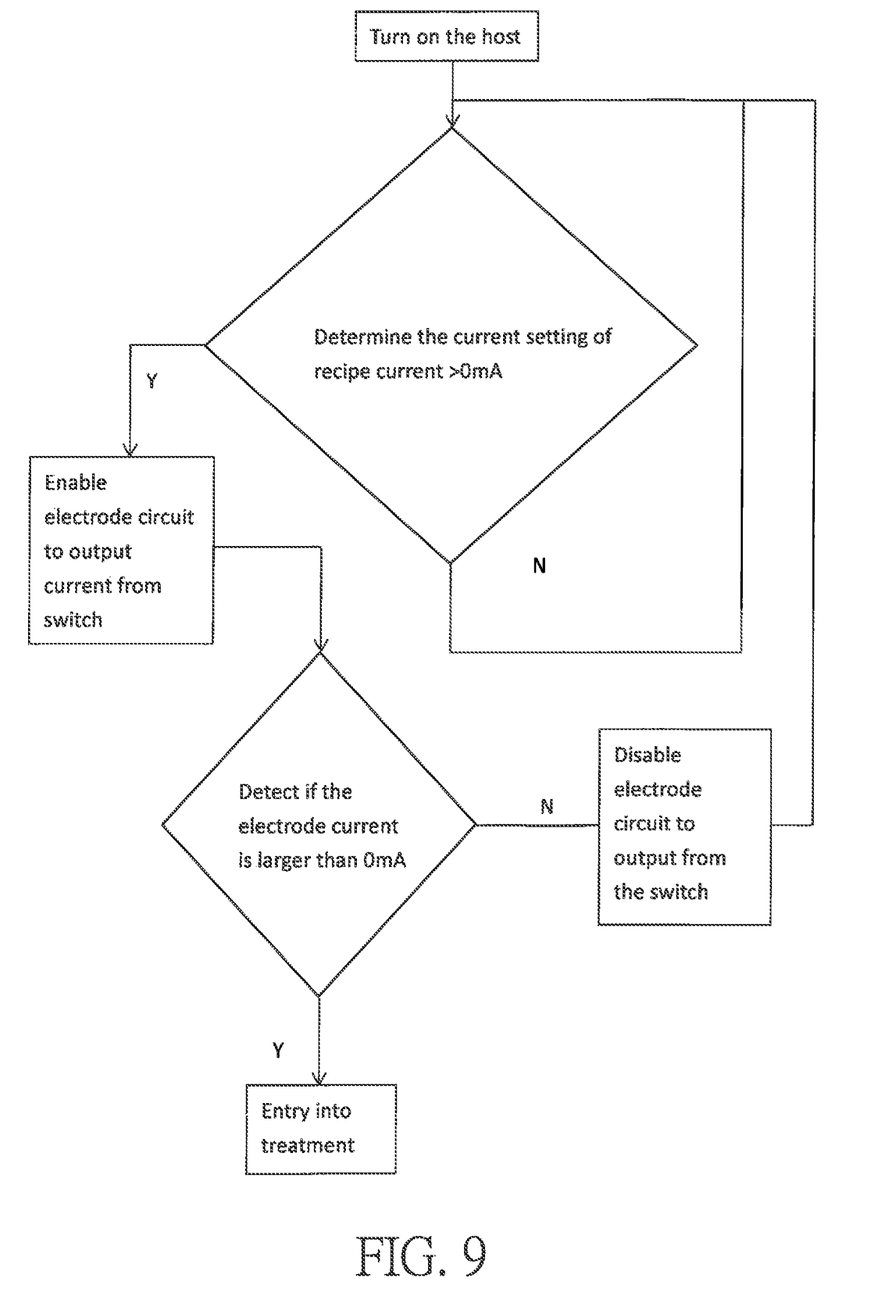
FIG. 9 is a block diagram of a detection procedure for a protection circuit of a preferred embodiment.

FIG. 8 is a block diagram of the system operation of the preferred embodiments, As shown in FIG. 8, the host and microprogram control unit (MCU) control the peripheral components and switches of the entire system. FIG. 9 is a block diagram of a detection procedure of the protection circuit. When the host is turned on, the control unit MCU will start to detect the current of electrode and report it to the host. First, the MCU will determine whether the current setting of recipe current is greater than 0 mA. Thereafter, when the current setting is greater than 0 mA, it will immediately enable the current output switch of the electrode circuit and detect, in a few seconds, whether the current is greater than 0 mA. The time for detection of a current may, by way of example and not limitation, be 1 second. If no current is generated, the current output switch of the electrode circuit will be disabled; if a current is generated, it means that the electrode is in contact with the target tissue, and the treatment will be continued.

Figure 10:
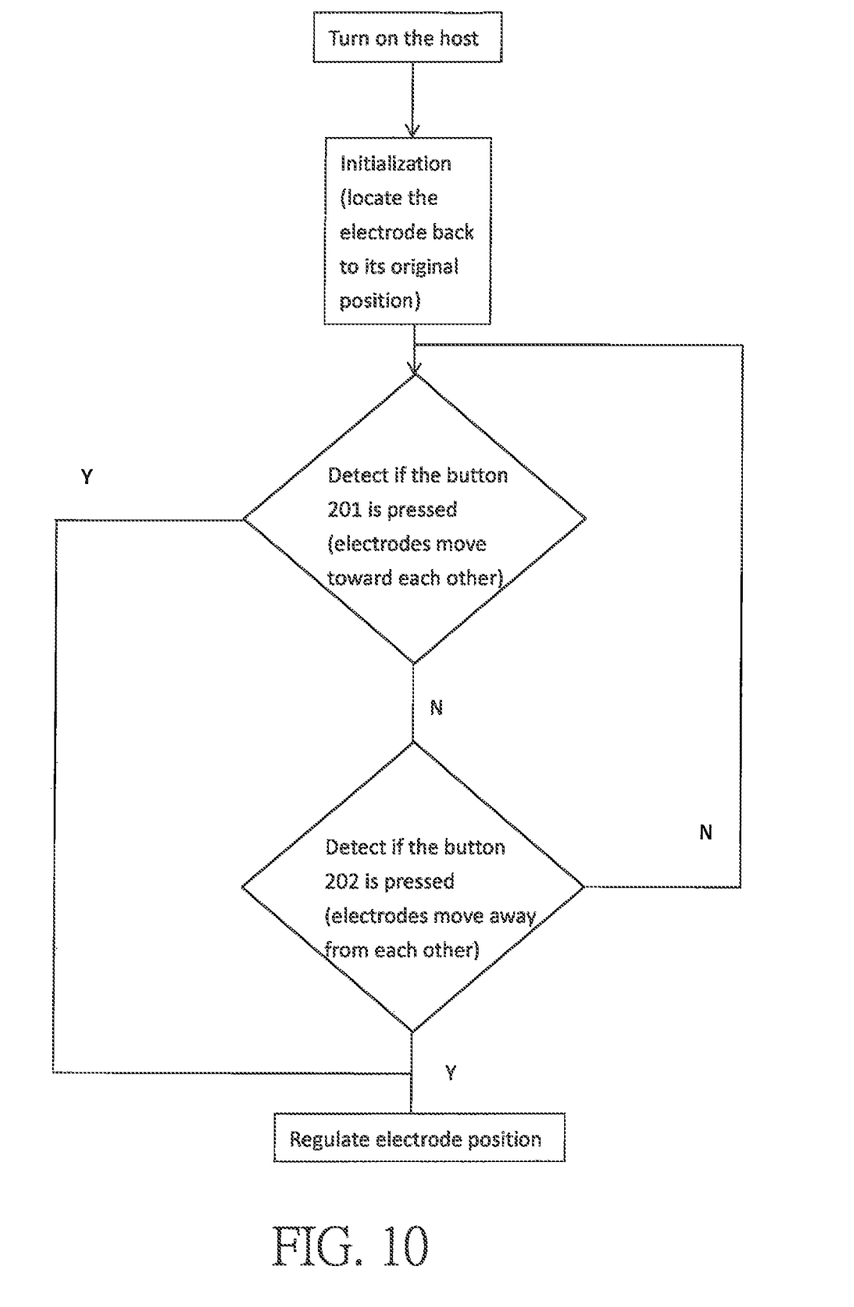
FIG. 10 is a block diagram of a regulation procedure of an electrode of a preferred embodiment.

FIG. 10 is a block diagram of a distance regulation procedure for the electrode of the preferred embodiments. Referring to FIGS. 1, 6, 7 and 10, when the host is turned on, the host will inform the MCU to initialize the electrode position and locate the electrode back to its original position. Thereafter, the MCU will detect whether the button 201 or the button 202 is pressed. When the button 201 is pressed, the electrodes will move toward each other, i.e., the second electrode 4 will be moved toward a position close to the first electrode 3. If the button 202 is pressed, the electrodes will move away from each other, i.e., the second electrode 4 will move in a direction away from the first electrode 3.

Figure 11:
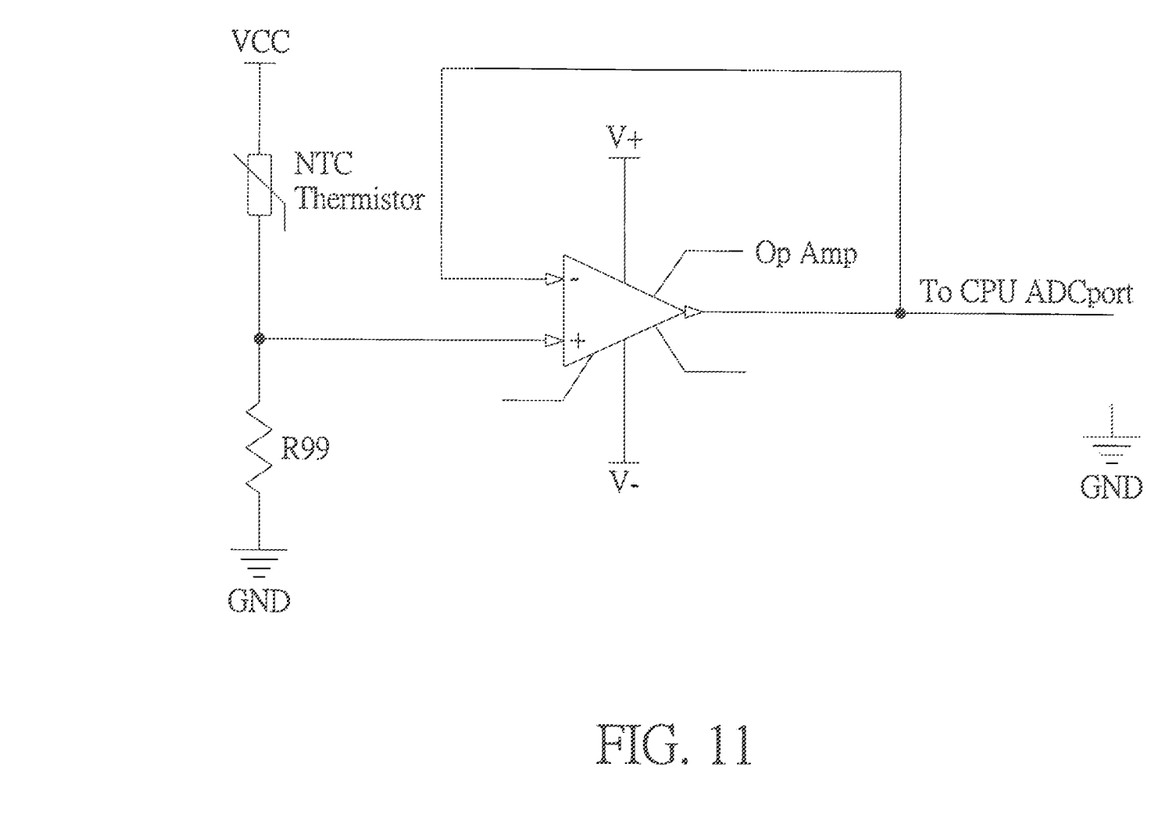
FIG. 11 is a circuit diagram of a temperature sensing unit of a preferred embodiment.

FIG. 11 is a circuit diagram of a temperature sensing unit that may be used in the preferred embodiments. Referring to FIGS. 4, 5, and 11, the temperature of the third surface is detected by temperature sensing unit 8, and a determination is made as to whether the cooling unit 7 needs to be activated to lower the temperature of the third surface 11 according to the detected temperature.

Figure 12:
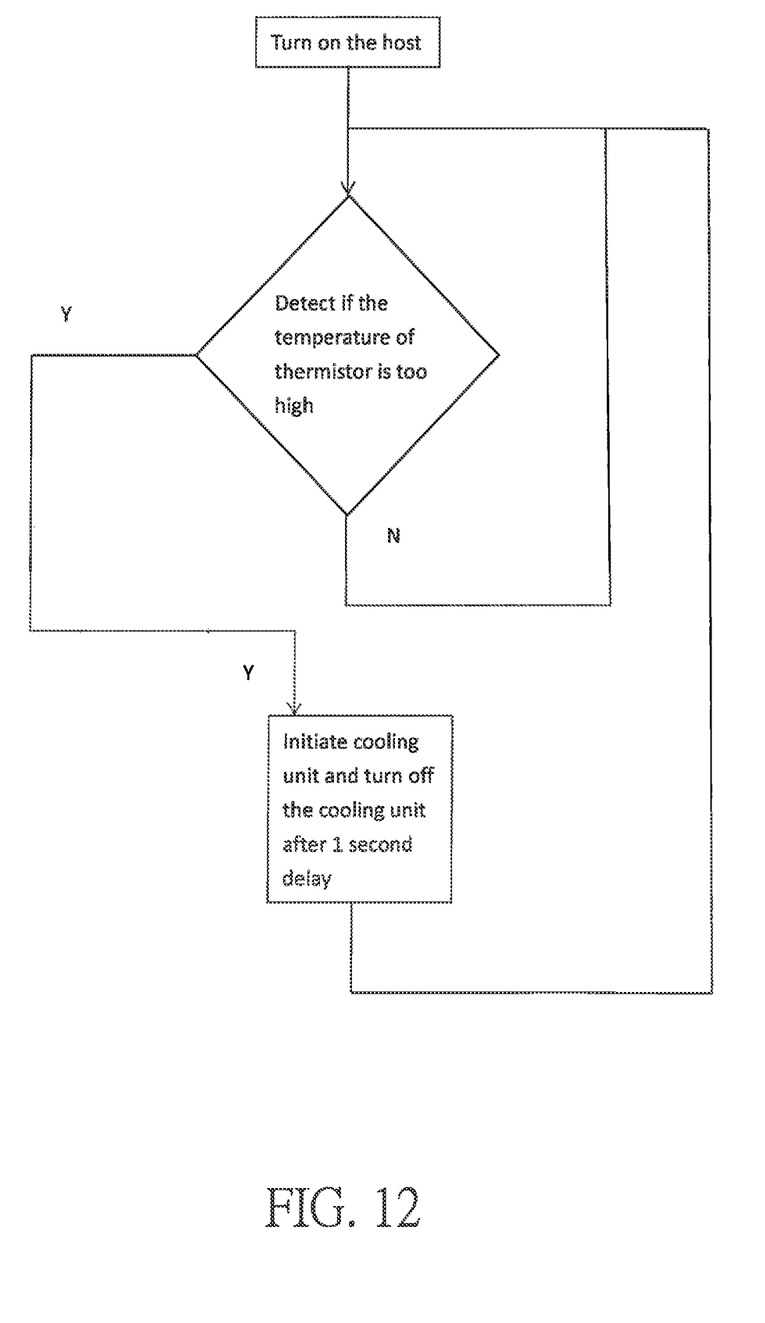
FIG. 12 is a block diagram of a cooling system procedure for a cooling chip of a preferred embodiment.

FIG. 12 is a block diagram of a cooling system procedure of a cooling chip that may be used in the preferred embodiments. Referring to FIGS. 4, 5 and 12, when the host is turned on, the MCU will start to detect the circuit voltage of the temperature sensing unit 8 and determine if the cooling unit 7 needs to be activated by the MCU's analog-to-digital converter (ADC) upon converting the detected parameter. When the detected temperature is too high, the third surface 11 of the subject in need 19 will be cooled down to prevent the surrounding tissue from thermal damage during the treatment.

The aforementioned embodiments are to be construed as merely illustrative and not limiting.

What is claimed is:

1. A non-perforative radio-frequency ablation system, comprising:
   an ablation device comprising:
      a housing having a first surface with a slot extended in the longitudinal direction of the housing;

a fixed electrode disposed on the first surface; and a movable electrode disposed in the slot on the first surface and adjacent to the fixed electrode; and a moving unit enclosed by the housing and electrically connected to the movable electrode and moving the movable electrode along the slot to regulate the distance between the movable electrode and the fixed electrode and regulate an ablation depth; and a cooling unit disposed on the first surface of the housing, between the fixed electrode and the movable electrode, and between the fixed electrode and a distal end of the slot; and a radio frequency generator connected to the ablation device for providing a radio frequency current to the fixed electrode and the movable electrode.

2. The radio-frequency ablation system according to claim 1, wherein the moving unit includes a ball screw.

3. The radio-frequency ablation system according to claim 1, wherein the cooling unit includes a cooling chip and/or refrigerant.

4. The radio-frequency ablation system according to claim 1, wherein the housing further comprises a second surface opposite to the first surface, and the ablation device further comprises a temperature sensing unit disposed on the first surface or the second surface.

5. The radio-frequency ablation system according to claim 4, wherein the temperature sensing unit is a thermistor or a resistance temperature detector (RTD).

6. The radio-frequency ablation system according to claim 1, wherein the housing further comprises a second surface opposite to the first surface, and the ablation device further comprises an ablation depth sensing unit disposed on the first surface or the second surface.

7. The radio-frequency ablation system according to claim 6, wherein the ablation depth sensing unit is an ultrasonic transducer.

* * * * *